(12) United States Patent
Hirabayashi et al.

(10) Patent No.: US 8,364,227 B2
(45) Date of Patent: Jan. 29, 2013

(54) BIOLOGICAL OPTICAL MEASUREMENT PROBE AND BIOLOGICAL OPTICAL MEASUREMENT INSTRUMENT THEREWITH

(75) Inventors: Yukiko Hirabayashi, Kokubunji (JP); Atsushi Ninomiya, Ome (JP); Yoshimi Kasai, Nagareyama (JP)

(73) Assignee: Hitachi, Ltd., Tokyo (JP)

( * ) Notice: Subject to any disclaimer, the term of this patent is extended or adjusted under 35 U.S.C. 154(b) by 1112 days.

(21) Appl. No.: 12/270,481

(22) Filed: Nov. 13, 2008

(65) Prior Publication Data
US 2009/0209837 A1    Aug. 20, 2009

(30) Foreign Application Priority Data
Feb. 20, 2008   (JP) .................................. 2008-038164

(51) Int. Cl.
*A61B 5/00*   (2006.01)
(52) U.S. Cl. .......................... 600/344; 600/310; 600/309
(58) Field of Classification Search .................. 600/344, 600/342, 310, 309
See application file for complete search history.

(56) References Cited

U.S. PATENT DOCUMENTS
2004/0054271 A1   3/2004   Maki et al.
2004/0077935 A1   4/2004   Hirabayashi et al.

FOREIGN PATENT DOCUMENTS
| EP | 1665979 | 6/2006 |
|---|---|---|
| JP | 2001-286449 | 10/2001 |
| JP | 2002-011012 | 1/2002 |
| JP | 2002-502653 | 1/2002 |
| JP | 2002-143169 | 5/2002 |
| JP | 2004-121702 | 4/2004 |
| JP | 2004313741 | 11/2004 |
| JP | 2006-158480 | 6/2006 |

OTHER PUBLICATIONS

Medical Physics, Dec. 1995, vol. 22, No. 12.
European Search Report dated Jun. 17, 2009.
T. Yamamoto, "Non-invasive Measurement of Language Function by Using Optical Topography", Part of the SPIE Conference on Optical Tomography and Spectroscopy of Tissue, San Jose, CA Jan. 1999, SPIE vol. 3597, pp. 230-237.

*Primary Examiner* — Jeffrey G Hoekstra
(74) *Attorney, Agent, or Firm* — Brundidge & Stanger, P.C.

(57) ABSTRACT

A probe which allows optical fiber fixing tools to be distributed substantially uniformly and symmetrically longitudinally or laterally and is easily fitted, even when a head part size of a subject changes is provided. A plurality of optical fiber fixing tools which fix incident optical fibers and detection optical fibers are arranged on a fixing part in a substantially straight line shape, a plurality of the fixing parts are included, the fixing parts are arranged so that its straight line direction is oriented in a substantially parietal direction, the optical fiber fixing tool on the fixing part and the optical fiber fixing tool on the adjacent different fixing part are connected by a connecting member, and the connecting member is made rotatable around the optical fiber fixing tool, whereby the probe can be fitted so that the optical fibers are arranged substantially symmetrically and uniformly longitudinally or laterally.

14 Claims, 21 Drawing Sheets

BIOLOGICAL OPTICAL MEASUREMENT PROBE AND BIOLOGICAL OPTICAL MEASUREMENT INSTRUMENT THEREWITH

CLAIM OF PRIORITY

The present application claims priority from Japanese patent application JP 2008-038164 filed on Feb. 20, 2008, the content of which is hereby incorporated by reference into this application.

BACKGROUND OF THE INVENTION

The present invention relates to a biological optical measurement technique for measuring a metabolite concentration of a living organism or its change in the concentration by using light, and particularly relates to a biological optical measurement probe for measuring the metabolite concentration of a head part of a subject, and a biological optical measurement instrument using the same.

The techniques of measuring change in a blood amount in a cerebral cortex accompanying brain activity at a number of points, and displaying the change in the blood amount as a moving image and a static image (biological optical measurement instruments) have been already proposed in "Medical Physics, vol. 22, No. 12, pp 1997-2005 (1995)" and "Proceedings of SPIE, vol. 3597, pp 230-237". Each of the arts uses a square probe in which incident optical fibers and detection optical fibers are alternately arranged in a tetragonal lattice shape.

Since it is difficult to bring the probe in the tetragonal lattice shape as described above into close contact with a substantially spherical head part, the following proposals have been already made.

(1) JP-A-2001-286449 describes a probe for a biological optical measurement instrument which has branched portions extended into branch shapes from a linking axis, and fits to the shape of a head part.

(2) JP-A-2002-143169 describes probes for a biological optical measurement instrument characterized in that linking parts of probes arranged in a lattice-shape rotate, and a holding part which holds each of the probes has elasticity.

(3) JP-A-2002-11012 describes a probe which covers an entire head part by filling a plurality of regions of the head part with tetragonal lattices, and gaps between them are filled with polygons.

(4) JP-A-2002-502653 describes an instrument for measuring a brain tissue of a subject in a non-invasive manner by arranging probes on a head part of the subject in a geometrical pattern.

(5) JP-A-2004-121702 describes a probe with incident optical fibers and detection optical fibers arranged in rhombic shapes, which covers an entire spherical head part by using four sets of the rhombic shapes, and is capable of displaying a portion corresponding to a brain by one image.

(6) JP-A-2006-158480 describes a probe which allows optical fibers located at the outer periphery of the probe to be placed at substantially the same position on a head part, for example, directly above the ears, even when the size of the head changes, by forming gaps by removing some of the connecting members connecting incident optical fibers and detection optical fibers and some of the optical fibers, and changing the distances between the optical fibers arranged around the gaps.

BRIEF SUMMARY OF THE INVENTION

The above described biological optical measurement instruments and probes have the following problems.

The above described probes arranged in the rhombic shape and lattice shape are in close contact with a substantially spherical head part, and can display the portion corresponding to the brain of at least the upper half of the head part with one image, but have the problem that when the size of the head part differs, the relative measurement position deviates, and the region of the brain which is measured differs. Specifically, if the head part is small, the probes can cover the region from a head top portion to the portion near the base of the ears, but in the case of a large head part, the probes can cover the head part only up to the significantly upper portion from the ears. It is said that a speech area controlling the language function exists in the part of the brain near the ears, and when the size of the head part changes, the speech area cannot be sometimes covered.

In the above described probe which allows size adjustment by forming gaps by removing some of the optical fibers, the above described problem is solved, but since all the connection parts rotate, it is difficult to fit the probe so that the optical fiber fixing tools are distributed to be substantially uniform and symmetrical longitudinally and laterally.

Specifically, the conventionally probes have the problem that it is difficult to make measurement at the same measurement position when a subject differs, for example, and have the problem that even in the case of the same subject, it is difficult to make measurement at the same measurement position when measurement is repeated, that is, it is difficult to obtain repeatability of the position.

The present invention is made to solve the above problems, and has an object to provide a biological optical measurement probe which does not allow distribution of optical fiber fixing tools from becoming ununiform at a time of fitting by handling some of the optical fiber fixing tools as integrated pieces and a biological optical measurement instrument using the same.

In order to attain the above-described object, the present invention has the following characteristics.

A plurality of optical fiber fixing tools which fix an incident optical fiber and a detection optical fiber are arranged on a fixing part in a substantially straight line shape, a plurality of the fixing parts are included, the fixing part is arranged so that its straight line direction is oriented in a substantially parietal direction, the optical fiber fixing tool on the fixing part and the optical fiber fixing tool on an adjacent different fixing part are connected with a connecting member, and the connecting member is made rotatable around the optical fiber fixing tool, whereby the probe can be fitted so that the optical fibers are arranged to be substantially symmetrical and uniform longitudinally or laterally (FIGS. 5 and 6 that will be described later).

Thus, the probe which can be fitted so that the optical fibers are arranged to be substantially symmetrical and uniform longitudinally and laterally can be provided.

A typical constitution example of the present invention will be listed hereinafter.

(1) A biological optical measurement probe of the present invention has a plurality of irradiation optical fibers for irradiating light to a subject, a plurality of detection optical fibers for detecting light which is irradiated from the irradiation optical fiber and propagates inside the subject, a plurality of fixing parts including a plurality of optical fiber fixing tools for fixing the irradiation optical fibers and the detection optical fibers respectively, and a connecting member which connects the optical fiber fixing tool on the fixing part and the optical fiber fixing tool on an adjacent different fixing part, respectively, wherein a plurality of optical fiber fixing tools on the fixing part are arranged equidistantly in a substantially straight line, the fixing part is arranged so that its straight line direction faces in a substantially parietal direction, connection is made so that distances between the optical fiber fixing tools on the adjacent different fixing parts connected by the connecting members become substantially equal, the distance between the optical fiber fixing tools is substantially equal to a distance between the adjacent optical fiber fixing tools on the same fixing part, and the connecting members are rotatable around the optical fiber fixing tools on the fixing parts.

(2) In the biological optical measurement probe in the above (1), the connecting member connecting the optical fiber fixing tools on the fixing part is constituted to be able to fix rotation around the optical fiber fixing tool.

(3) In the biological optical measurement probe in the above (1) and (2), the fixing part is constituted so that three or more optical fiber fixing tools can be arranged on the fixing part.

(4) In the biological optical measurement probe in the above (1) to (3), the fixing parts are arranged substantially parallel with each other.

(5) In the biological optical measurement probe in the above (1) to (3), the fixing parts are arranged substantially radially.

(6) In the biological optical measurement probe in the above (1) to (3), a plurality of the fixing parts are arranged parallel with one another, a plurality of sets of the plurality of fixing parts arranged substantially parallel with one another are arranged substantially radially.

(7) In the biological optical measurement probe in the above (1) to (6), the fixing part is bonded to a cloth material with elasticity.

(8) In the biological optical measurement probe in the above (1) to (6), a weave texture in a direction in which a resin net material does not expand or contract is used as the fixing part.

(9) A biological optical measurement instrument according to the present invention has a plurality of irradiation optical fibers for irradiating light to a subject, a plurality of detection optical fibers for detecting light which is irradiated from the irradiation optical fiber and propagates inside the subject, a plurality of fixing parts including a plurality of optical fiber fixing tools for fixing the irradiation optical fibers and the detection optical fibers respectively, and a connecting member which connects the optical fiber fixing tool on the fixing part and the optical fiber fixing tool on an adjacent different fixing part, respectively, wherein a plurality of optical fiber fixing tools on the fixing part are arranged substantially equidistantly in a substantially straight line, the fixing part is arranged so that its straight line direction faces in a substantially parietal direction, connection is made so that distances between the optical fiber fixing tools on the adjacent separate fixing parts connected by the connecting members become substantially equal, a distance between the optical fiber fixing tools is substantially equal to a distance between the adjacent optical fiber fixing tools on the same fixing part, and the connecting member is rotary and variable around the optical fiber fixing tool on the fixing part.

(10) In the biological optical measurement instrument in the above (9), an operation part is configured to calculate a metabolite concentration inside the subject with a substantially middle point position between the irradiation optical fiber and the detection optical fiber as a measurement point, based on a signal detected by the probe.

According to the present invention, the biological optical measurement probe which is easily fitted so that the incident and detection optical fibers become substantially uniform or symmetrical longitudinally or laterally and the biological optical measurement instrument using the same can be realized.

Further, the probe which is easily put on and facilitates positioning of the position of the probe, irrespective of small or large of the size of the head, and the biological optical measurement instrument using the same can be realized.

Other objects, features and advantages of the invention will become apparent from the following description of the embodiments of the invention taken in conjunction with the accompanying drawings.

DETAILED DESCRIPTION OF THE INVENTION

Hereinafter, embodiments of the present invention will be described in detail with reference to the drawings.

Figure 1A:
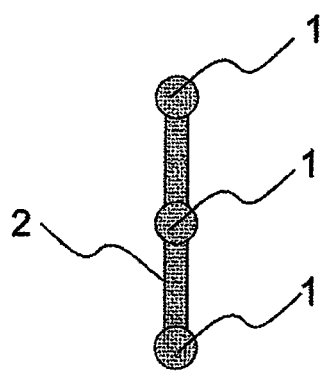
FIGS. 1A to 1C are developments showing a fixing part (FIG. 1A), a constitution of a connecting member (FIG. 1B), and a first arrangement example (FIG. 1C) of a biological optical measurement probe which is one embodiment of the present invention.
Figure 1B:
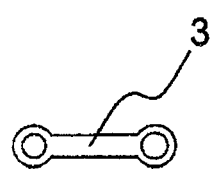
Figure 1C:
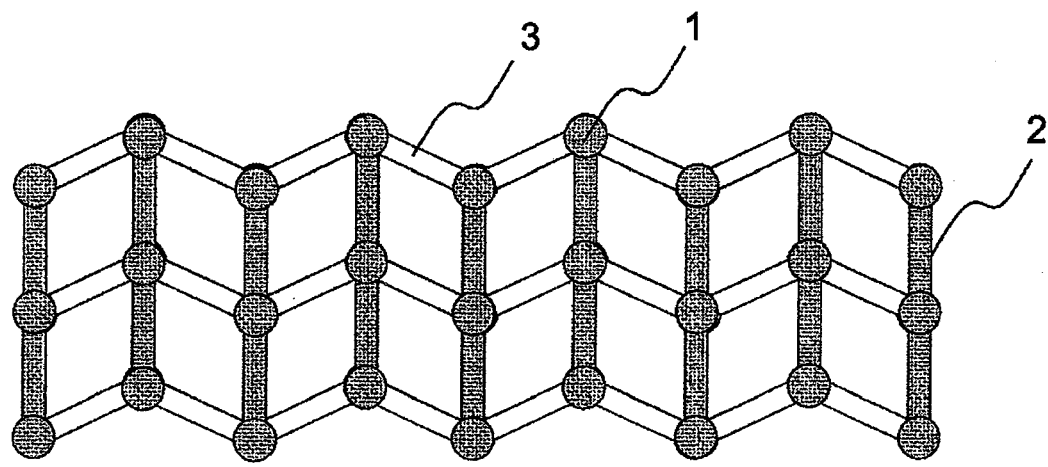

FIG. 1C is a development showing an arrangement constitution of a biological optical measurement probe which is one embodiment of the present invention. FIG. 1A shows a fixing part constituting the biological optical measurement probe of the present invention. Optical fiber fixing tools 1 which fix incident optical fibers or detection optical fibers are substantially equidistantly arranged on a fixing part 2. The fixing tools 1 on the adjacent different fixing parts 2 are connected by a connecting member 3 shown in FIG. 1B, and the adjacent fixing parts 2 are arranged substantially equidistantly. The connecting member 3 is made of a material which does not contract or expand, and keep gaps between the fixing tools 1 on the adjacent separate fixing parts 2 substantially constant. The connecting member 3 can rotate with the position of the optical fiber fixing tool 1 as the support point, and allows the probe to fit to a head part along a shape of the round head part. For the material, the materials which do not have much elasticity but are relatively soft, such as hard silicon rubber, resins and for example, are cited.

The probe is manufactured by adjusting the length of the connecting member 3 and the length of the fixing part 2 so that the distance between the adjacent optical fiber fixing tools 1 on the same fixing part 2, and the distance between the fixing tools 1 which are on the adjacent different fixing parts 2 and are connected with the connecting member 3 become substantially equal. The distance is set at 3 cm for the probe for an adult, and set at 2 cm or 3 cm for the probes for a child or an infant, or a newborn. There is naturally no problem if the distance is set at the other values.

FIG. 1A and 1C show an example in which three of the fixing tools 1 are connected, but the number of the fixing tools 1 may be any number if it is three or more. The number of the connected fixing tools is desirably an odd number such as 3, 5, 7 and the like. The reason of it is that if the odd-numbered fixing tools are adopted, the connection in such a manner as "the incident optical fiber to the detection optical fiber to the incident optical fiber" can be made, and one detection optical fiber can be used more effectively.

The reason why the fixing tools are fixed in the vertical direction is that there is less individual difference in the vertical direction of a head as compared with the head circumference. When the fixing tools 1 are not fixed in all the directions, reproducibility of the fitting position is difficult to obtain, but when they are fixed in the lateral direction (head circumference, at the time of fitting), reproducibility of the fitting position is difficult to obtain, since the individual difference in size of the head is large.

Further, in the case of the shapes as shown in FIGS. 4 to 9, if the probes are fixed in the lateral direction, there arises the problem of capability and incapability of putting on the probes due to difference in size of the head.

It is not until the probe can be freely changed in size in the head circumference direction and is fixed in the vertical direction as in the present invention that the probe becomes easy to put on irrespective of the size of the head, and positioning of the position of the probe can be easily performed.

Figure 2:
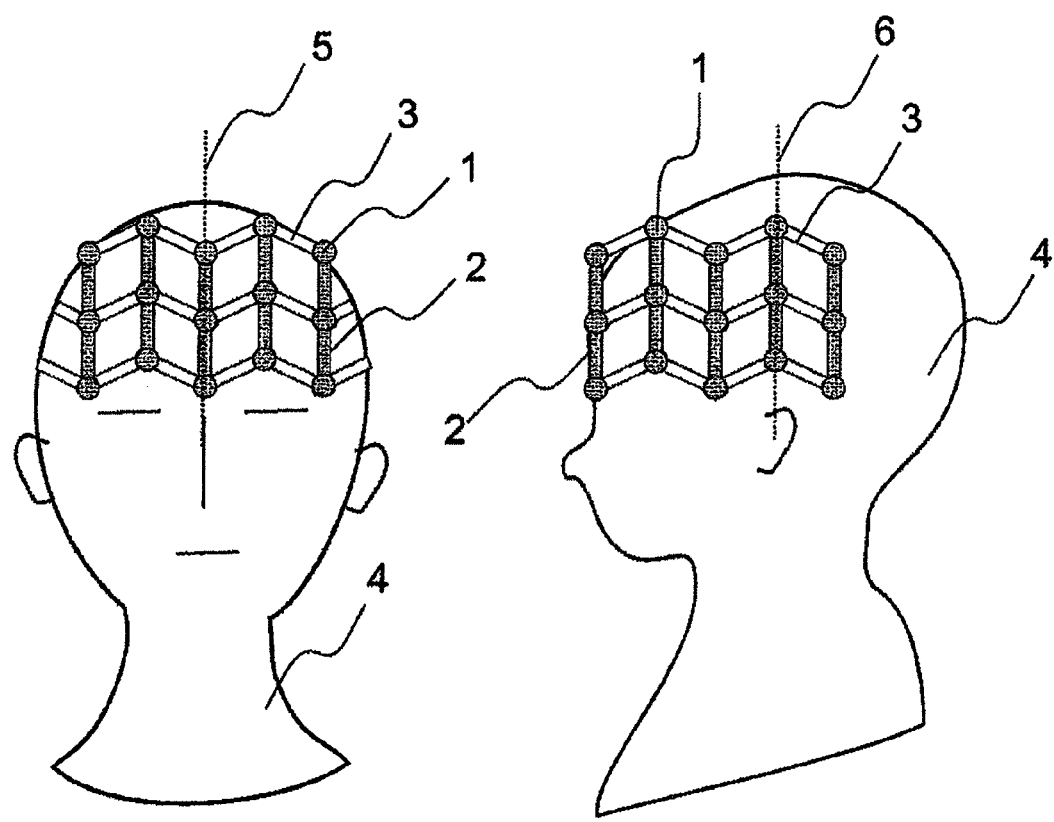
FIG. 2 is a view showing a state in which the probe of FIGS. 1A to 1C is fitted to a subject having a small head.

FIG. 2 shows a state in which the biological optical measurement probe which is one embodiment of the present invention shown in FIGS. 1A to 1C is fitted to a subject 4. This is the case of a relatively small head. The probe is fitted so that a long axis direction of the fixing part 2 becomes substantially the same as a direction from a parietal to a chin. The probe is fitted so that, for example, the fixing part 2 located at the center of the probe is superimposed on an alignment line 5 passing from the parietal to the base of the nose, and the fixing parts 2 located at the ends are superimposed on alignment lines 6 connecting the parietal to the ear holes. When the head is small, the connecting members 3 rotate around the optical fiber fixing tools 1, and are disposed so that the gaps between the fixing tools 1 become narrow and the connecting members 3 form shapes like arrow heads, as shown in FIG. 2.

Figure 3:
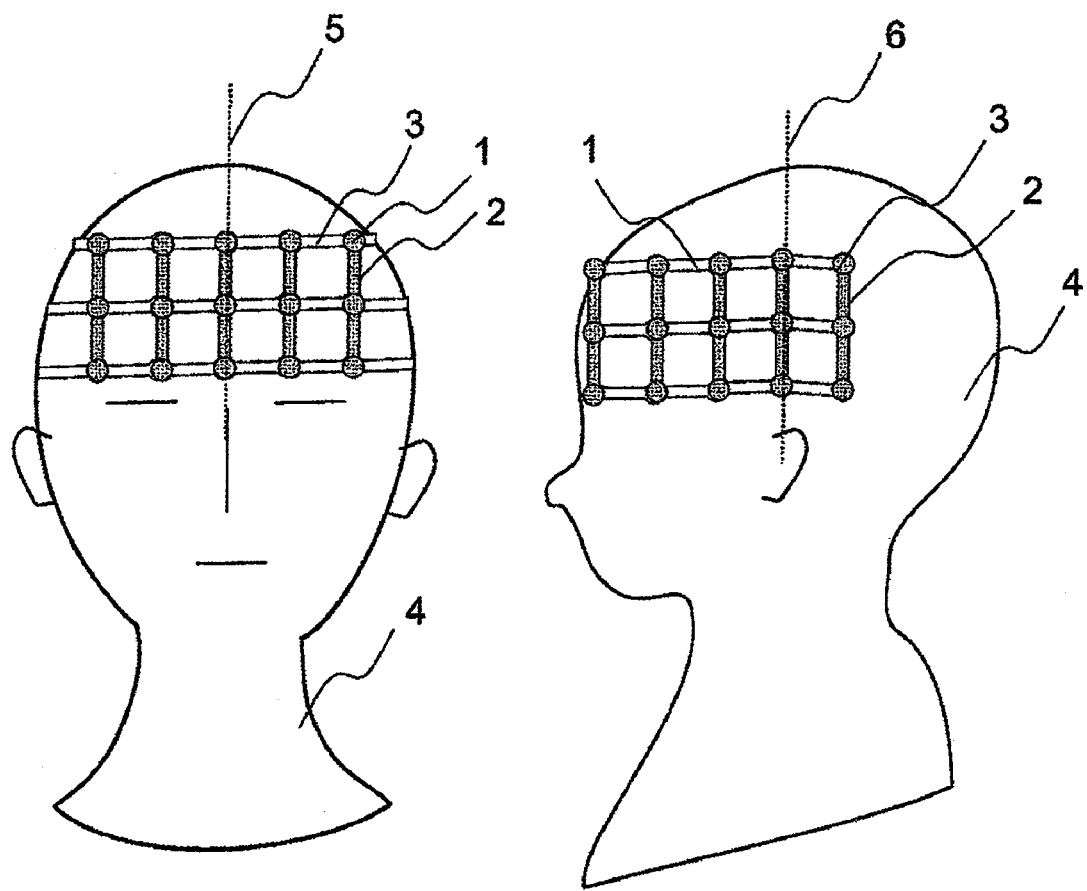
FIG. 3 is a view showing a state in which the probe of FIGS. 1A to 1C is fitted to a subject having a large head.

FIG. 3 shows a state in which the biological optical measurement probe which is one embodiment of the present invention shown in FIG. 1 is fitted to the subject 4 as in FIG. 2. However, in this case, the head is relatively large. As in the case of FIG. 2, the probe is fitted so that the long axis direction of the fixing part 2 becomes substantially the same as the direction from the parietal to the chin. As in FIG. 2, the probe is fitted so that the fixing part 2 located in the center of the probe is superimposed on the alignment line 5 passing from the parietal to the base of the nose, and the fixing parts 2 located at the ends are superimposed on the alignment lines 6 connecting the parietal and the ear holes. When the head is large, the connecting members 3 rotate around the optical fiber fixing tools 1, and are disposed so that the gaps between the fixing tools 1 become wide and the connecting members 3 are in the shapes aligned in substantially straight lines.

Figure 4:
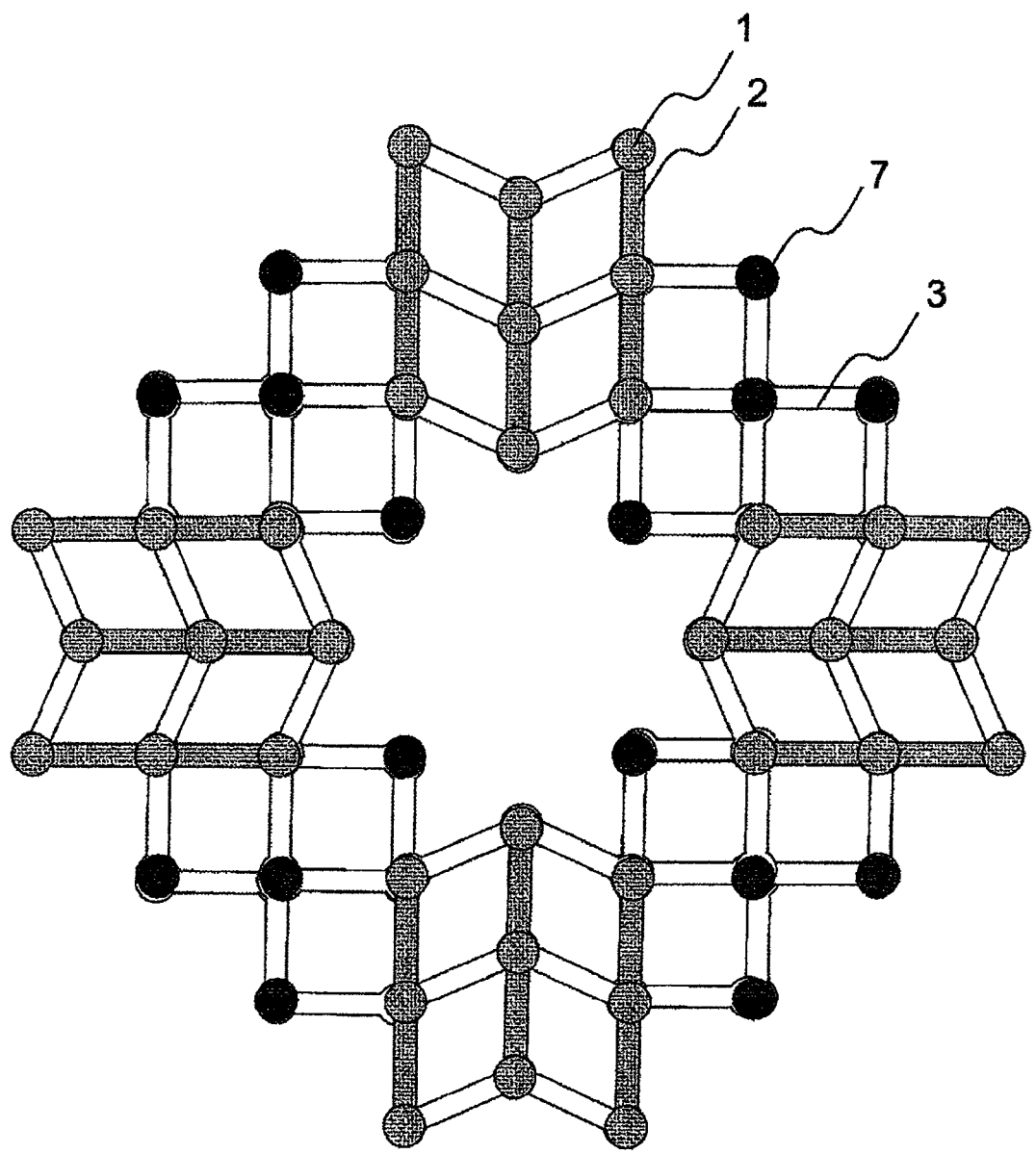
FIG. 4 is a development showing a second arrangement example of the probe according to the present invention.

FIG. 4 is a development showing an arrangement constitution of a biological optical measurement probe which is another embodiment of the present invention. The optical fiber fixing tools 1 which fix incident optical fibers or detection optical fibers are substantially equidistantly arranged on the fixing part 2. In this case, three fixing tools 1 are arranged on each of the fixing parts 2, and the fixing tools 1 on the adjacent different fixing parts 2 are connected by the connecting members 3, and the adjacent fixing parts 2 are arranged substantially equidistantly. The connecting member 3 is made of a material which does not expand or contract, and keeps a gap between the fixing tools 1 on the adjacent different fixing parts 2 substantially constant. The connecting member 3 can rotate with the position of the optical fiber fixing tool 1 as the support point. Four sets of the three fixing parts 2 arranged side by side are radially arranged. The reason why the four sets are arranged is that the regions of the head which are mainly desired to be measured are four areas that are a frontal lobe, an occipital lobe and left and right temporal lobes. As in FIG. 4, by arranging the four sets, the effect of facilitating positioning for the above described four areas is provided. The sets of the fixing parts 2 are connected by a plurality of connecting members 3, and a plurality of single optical fiber fixing tools 7 which are not on the fixing parts. The connecting members 3 are rotatable around the single optical fiber fixing tools 7, and therefore, in combination with the effect of the sets of the fixing parts 2, the connecting members 3 allow the probe to fit to a head part along a shape of the round head part. For the material, for example, a hard silicon rubber, resin, gel and the like are cited.

The probe is manufactured by adjusting the length of the connecting member 3 and the length of the fixing part 2 so that the distance between the adjacent optical fiber fixing tools 1 on the same fixing part 2, the distance between the fixing tools 1 which are on the adjacent different fixing parts 2 and are connected by the connecting member 3, the distance between the optical fiber fixing tool 1 on the fixing part 2 and the single optical fiber fixing tool 7 connected by the connecting member 3, and the distance between the single optical fiber fixing tools 7 connected by the connecting member 3 become substantially equal. The distance is set at 3 cm for the probe for an adult, and set at 2 cm or 3 cm for the probes for a child or an infant, or a newborn. There is naturally no problem if the distance is set at the other values.

Figure 5:
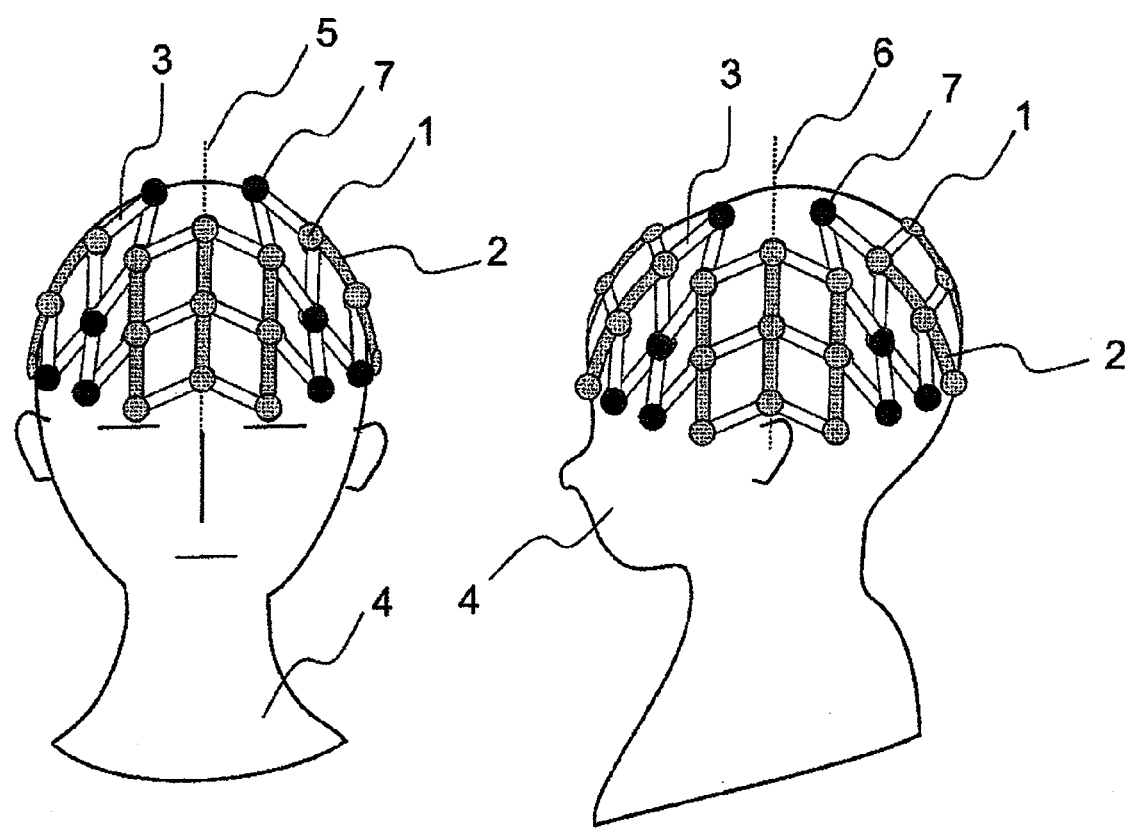
FIG. 5 is a view showing a state in which the probe of FIG. 4 is fitted to a subject having a small head.

FIG. 5 shows a state in which the biological optical measurement probe which is another embodiment of the present invention shown in FIG. 4 is fitted to the subject 4. This is the case of a relatively small head. The probe is fitted so that the long axis direction of the fixing part 2 becomes substantially the same as the direction from a parietal to a chin and ears. The probe is fitted so that, for example, the fixing part 2 located at the center of the frontal portion, of the probe is superimposed on the alignment line 5 passing from the parietal to the base of the nose, and the fixing parts 2 located at the centers of the temporal portions are superimposed on the alignment lines 6 connecting the parietal to the ear holes. When the head is small, the connecting members 3 rotate around the optical fiber fixing tools 1, and are arranged so that the gaps between the fixing tools 1 become narrow, the gaps between the single optical fiber fixing tools 7 which are not connected by the connecting members 3 become narrow, and the connecting members 3 form shapes like arrow heads, as shown in FIG. 5.

Figure 6:
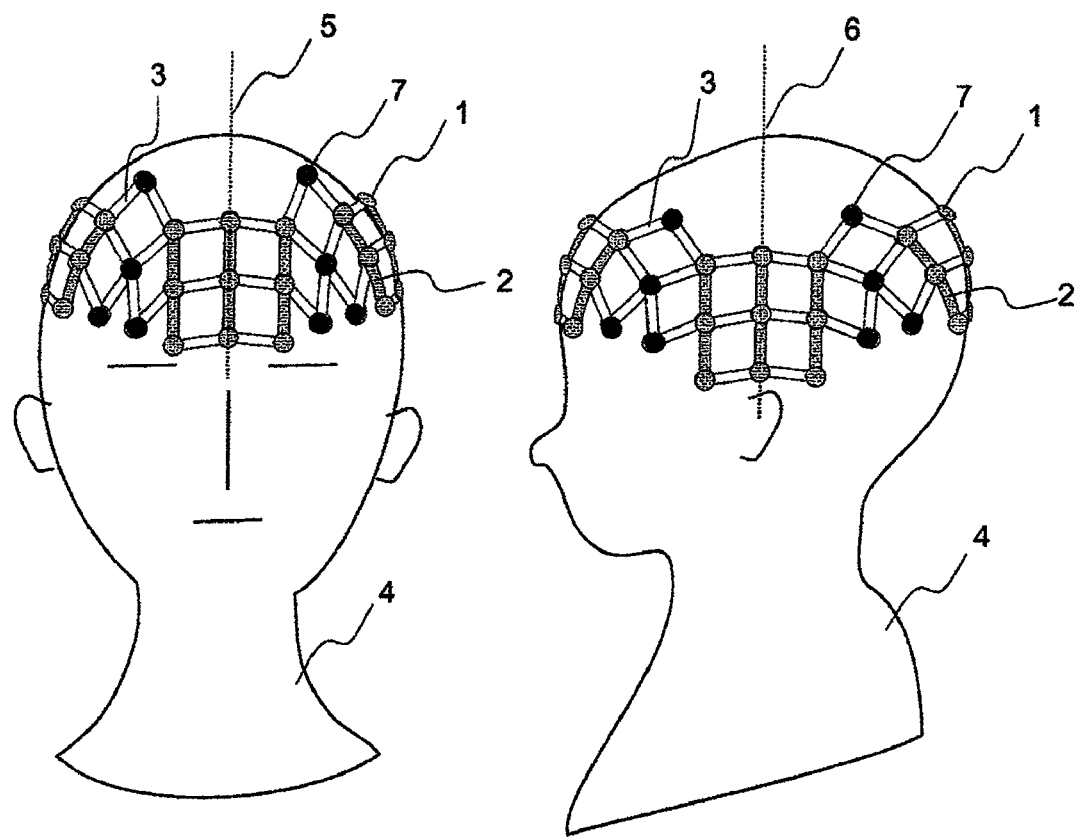
FIG. 6 is a view showing a state in which the probe of FIG. 4 is fitted to a subject having a large head.

FIG. 6 shows a state in which the biological optical measurement probe which is another embodiment of the present invention shown in FIG. 4 is fitted to the subject 4 as in FIG. 5. However, this is the case of a relatively large head. As in the case of FIG. 5, the probe is fitted so that the long axis direction of the fixing part 2 becomes substantially the same as the direction from the parietal to the chin and the ears. As in FIG. 5, the probe is fitted so that the fixing part 2 located in the center of the frontal portion, of the probe is superimposed on the alignment line 5 passing from the parietal to the base of the nose, and the fixing parts 2 located at the centers of the temporal portions are superimposed on the alignment lines 6 connecting the parietal and the ear holes. When the head is large, the connecting members 3 rotate around the optical fiber fixing tools 1, and are arranged so that the gaps between the fixing tools 1 become wide, and the gaps between the single optical fiber fixing tools 7 which are not connected by the connecting members 3 become wide.

Figure 7:
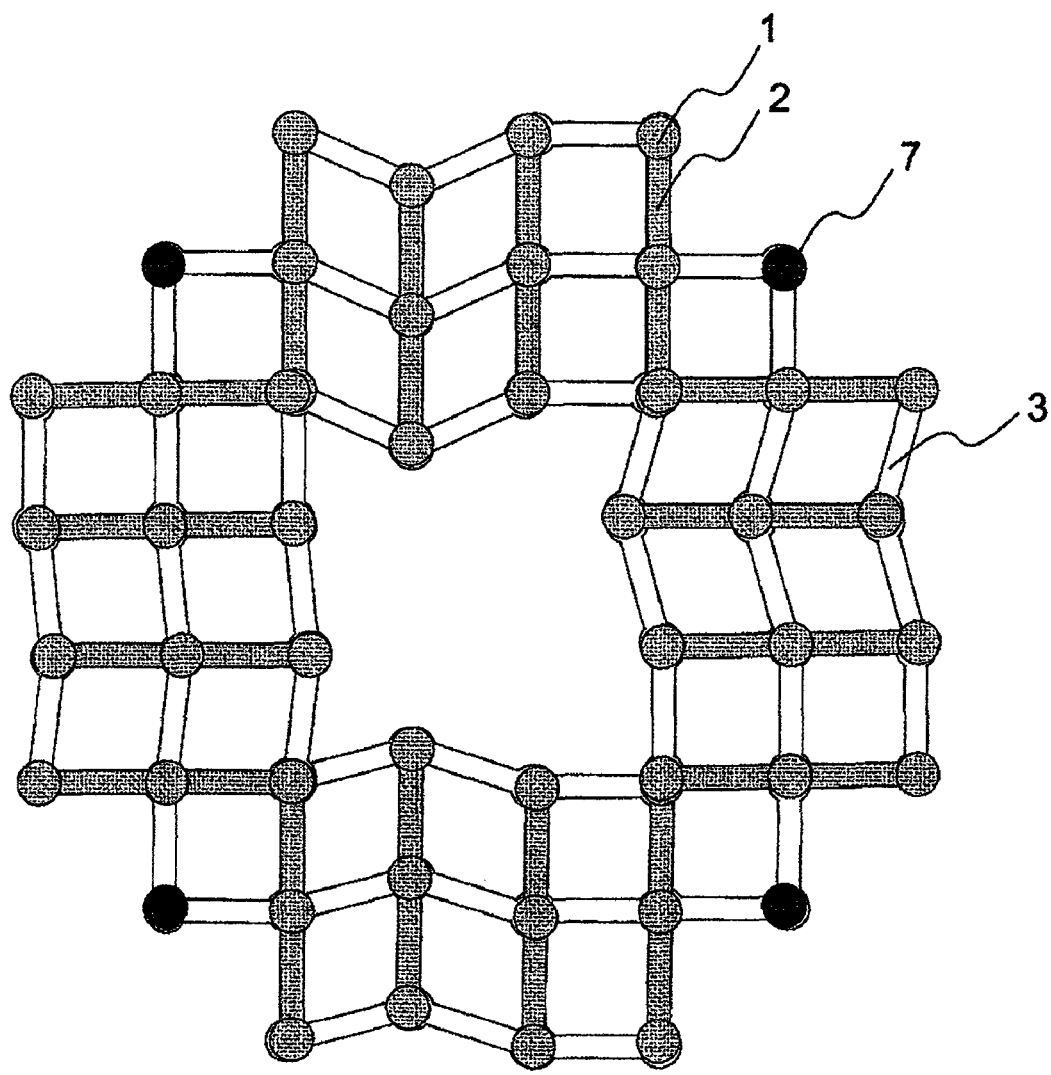
FIG. 7 is a development showing a third arrangement example of the probe according to the present invention.

FIG. 7 is a development showing an arrangement constitution of a biological optical measurement probe which is still another embodiment of the present invention. Four fixing parts 2 make a set, and four sets are arranged radially. The number of fixing parts 2 which make a set may be, for example, one, two, five or more, other than three or four.

Figure 8:
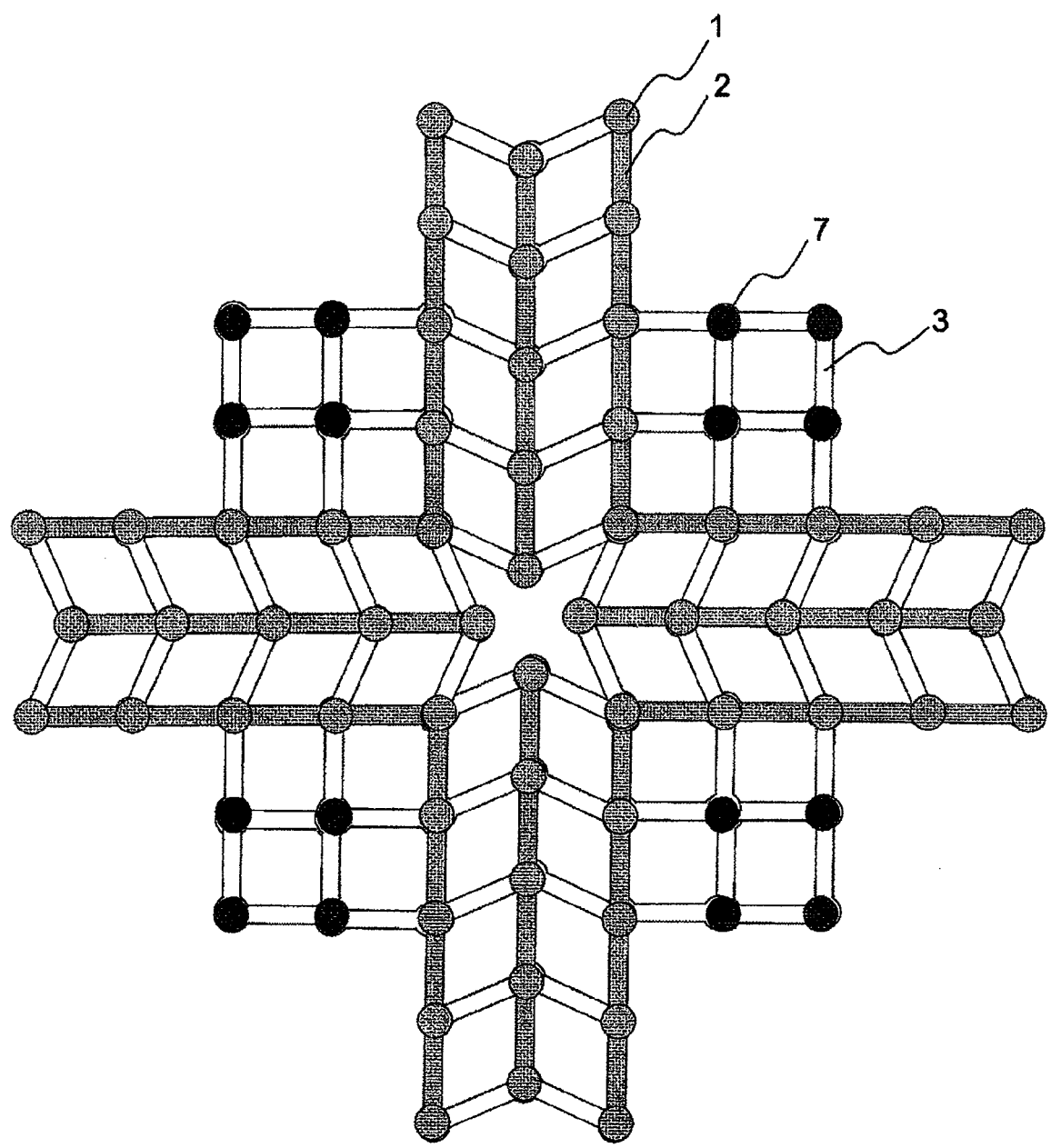
FIG. 8 is a development showing a fourth arrangement example of the probe according to the present invention.

FIG. 8 is a development showing an arrangement constitution of a biological optical measurement probe of yet another embodiment of the present invention. The six optical fiber fixing tools 1 are arranged on the fixing part 2. The number of optical fiber fixing tools arranged on the fixing part 2 may be three, six, and any number if only it is not smaller than three.

Figure 9:
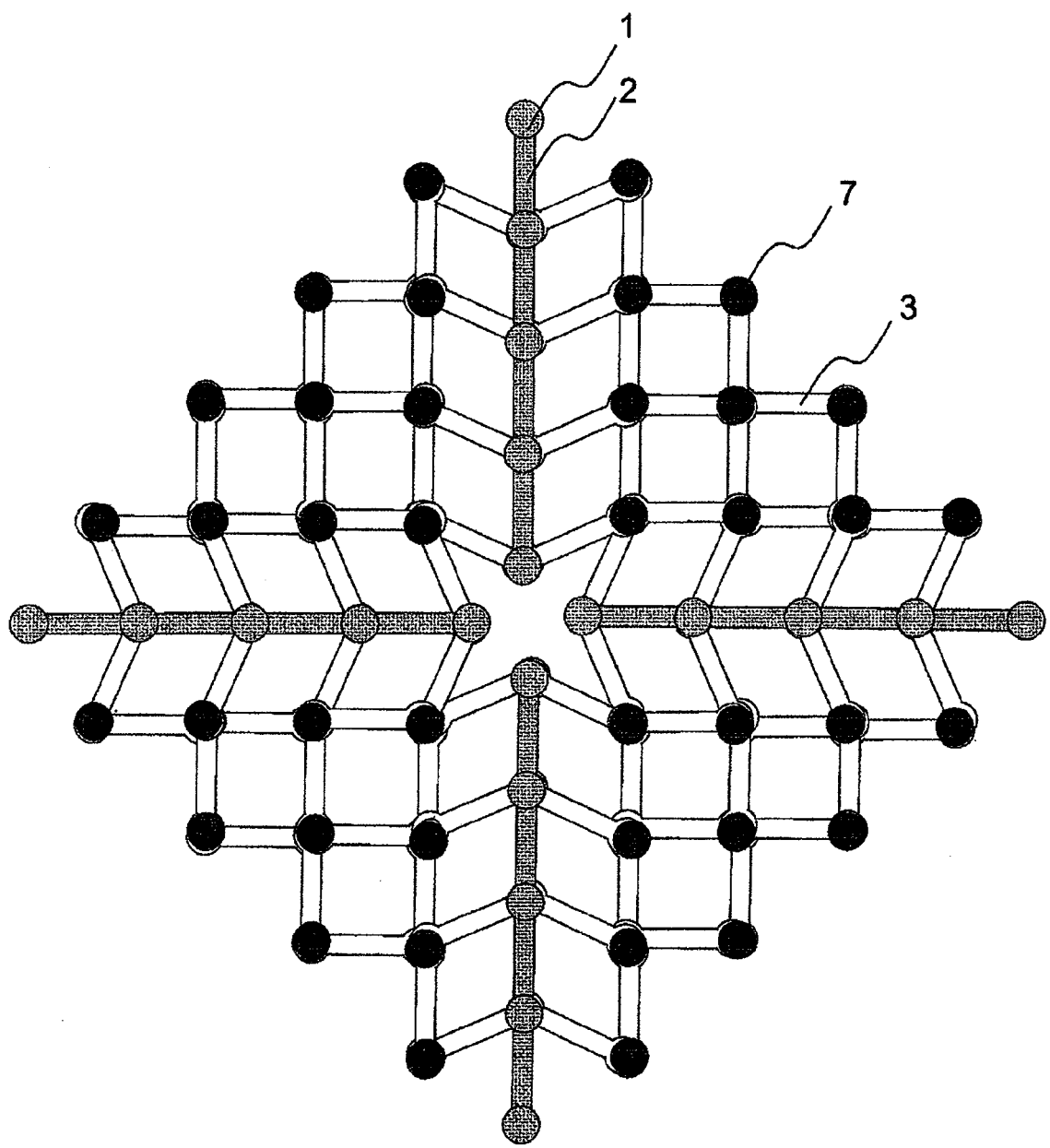
FIG. 9 is a development showing a fifth arrangement example of the probe according to the present invention.

FIG. 9 is a development showing an arrangement constitution of a biological optical measurement probe which is still another embodiment of the present invention. The four fixing parts 2 are radially arranged.

Figure 10A:
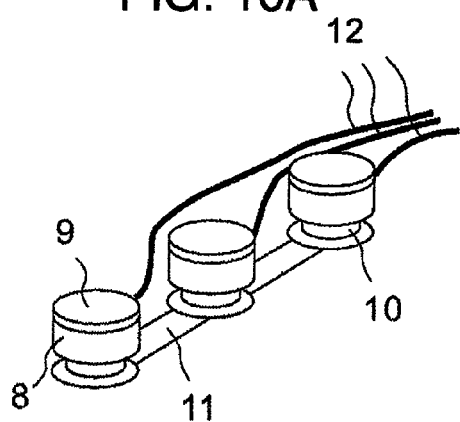
FIGS. 10A to 10D are conceptual views of the fixing part (FIG. 10A), a fixing part used for a different portion (FIG. 10B), a single optical fiber fixing tool (FIG. 10C), and a component shape of the connecting member (FIG. 10D) constituting the probe according to the present invention.
Figure 10B:
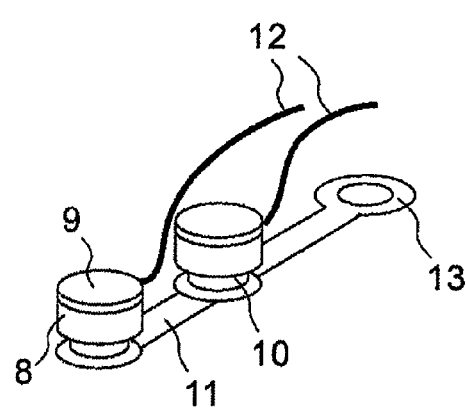
Figure 10C:
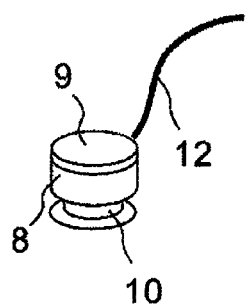
Figure 10D:
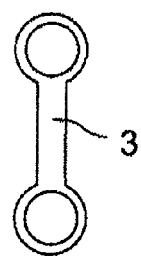

FIGS. 10A to 10D are conceptual views showing examples of the shapes of components constituting the biological optical measurement probe which is one embodiment of the present invention. FIG. 10A shows the constitution of the optical fiber fixing tools 1 and the fixing part 2. The optical fiber fixing tool 1 is constituted of a socket 8 and a lid 9. In the socket 8, a groove 10 in which a ring portion of the connecting member 3 shown in FIG. 10D is fitted is made. The socket is fixed onto a base portion 11. An optical fiber 12 is inserted into the socket 8, and is fixed by being covered with the lid 9. The lid 9 and the socket 8 may be bonded to each other. FIG. 10B shows a state in which one of the three sockets 8 is replaced with a ring 13 similar to that of the connecting member 3. This is used for the portion where the fixing parts 2 are directly connected without using the connecting member 3, in each of, for example, FIGS. 7 and 8. Accordingly, with the components connected, three or more optical fiber fixing tools 1 are arranged on the fixing part 2. FIG. 10C is a constitution of the single optical fiber fixing tool 7. Similarly, it is constituted of the socket 8 and the lid 9, the socket 8 has the groove 10, and the optical fiber 12 inserted in the socket 8 is fixed with the lid 9. Similarly, the socket 8 and the lid 9 may be bonded to each other.

Figure 11:
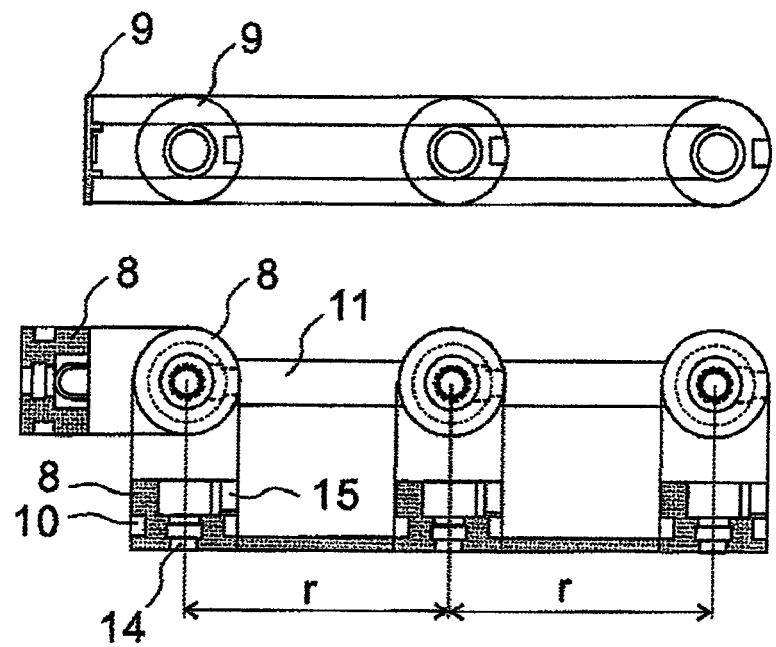
FIG. 11 is a sectional view of the components of FIGS. 10A to 10D.
Figure 12:
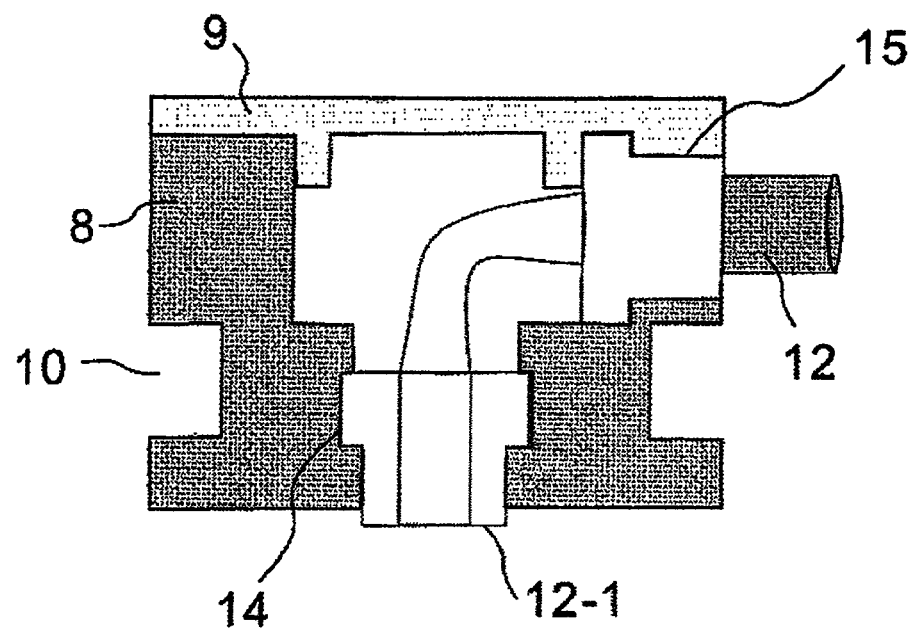
FIG. 12 is a sectional view of a state in which an optical fiber is inserted into the optical fiber fixing tool, of the components of FIG. 10.

FIG. 11 shows one example of a sectional view of the components constituting the optical fiber fixing tool 1 and the fixing part 2 shown in FIGS. 10A to 10D. When the components are constituted of silicon rubber or the like, the socket 8 and the base portion 11 may be integrally molded as shown in FIG. 11. The lid 9 is separately molded. As shown in FIG. 12, a tip end surface 12-1 of the optical fiber, which emits and receives light, is inserted into an optical fiber insertion port 14 which is opened at a lower portion of the socket 8, and the optical fiber 12 is fixed so that the tip end surface 12-1 is at substantially the same height as a bottom surface of the socket 8, or is slightly projected from the bottom surface. The optical fiber 12 which is inserted in the fiber insertion port 14 is bent inside the socket 8, and is led outside from an optical fiber lead-out port 15. From above this, the optical fiber 12 is fixed with the lid 9. Recesses and projections may be formed in accordance with the shapes of the optical fiber inside the fiber insertion port 14 and the fiber lead-out port 15 so that the optical fiber does not remove. A recess and projection may be also formed in the lid 9 so that the lid 9 hardly slips or removes when it is fitted in the socket 8. Further, the socket 8 and the lid 9 may be bonded to each other. A distance r between the sockets is set at, for example, 2 or 3 centimeters. It may be set at other numerical values.

FIG. 12 is a sectional view of a state in which the optical fiber 12 is inserted into the optical fiber insertion port 14 of the socket 8, the optical fiber 12 is led out from the optical fiber lead-out port 15, and the lid 9 is put on. In this case, the optical fiber tip end surface 12-1 is projected from the bottom surface of the socket 8. When it is projected, the projected length is set at about 1 mm or less. Depending on the case, the heights of the bottom surface of the socket 8 and the tip end surface 12-1 may be made substantially equal.

Figure 13A:
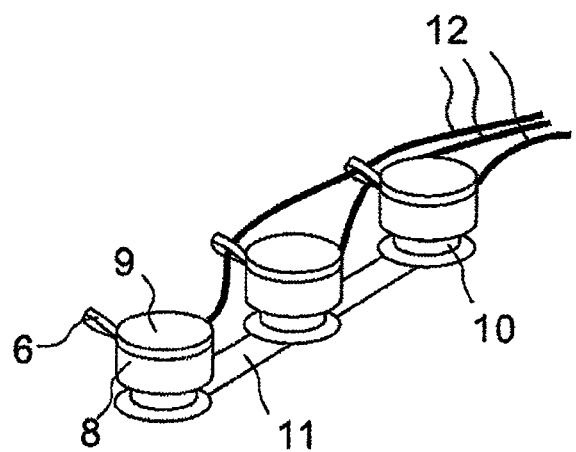
FIGS. 13A to 13D are conceptual views of the fixing part (FIG. 13A), a fixing part used for a different portion (FIG. 13B), a single optical fiber fixing tool (FIG. 13C), and a component shape of the connecting member (FIG. 13D) of another embodiment constituting the probe according to the present invention.
Figure 13B:
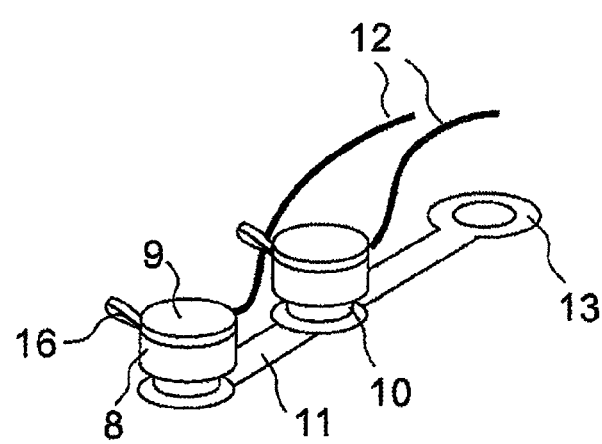
Figure 13C:
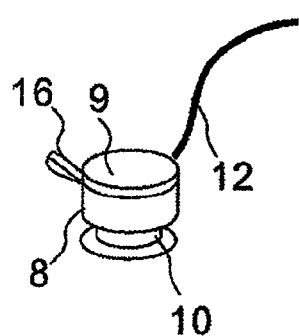
Figure 13D:
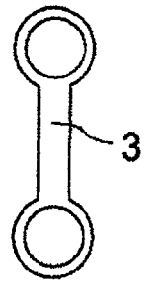

FIGS. 13A to 13D are conceptual views showing other examples of the shapes of components constituting the biological optical measurement probe which is one embodiment of the present invention. The difference from the embodiment in FIGS. 10A to 10D is that the socket 8 and the lid 9 are connected by a retaining member 16. FIG. 13A shows the constitution of the optical fiber fixing tools 1 and the fixing part 2 similar to those in FIG. 10A. In the state in which the lid 9 is fitted in the socket 8, the retaining member 16 is in a ring shape as shown in FIG. 13A. The optical fibers 12 located nearby may be bound by the ring of the retaining member 16. By binding the optical fibers 12, the optical fibers 12 can be made difficult to entangle. FIG. 13B shows that one of the sockets 8 is replaced with the ring 13, and this is used for the position similar to FIG. 10B. FIG. 13C shows the single optical fiber fixing part similar to FIG. 10C. FIG. 13D shows the connecting member 3.

Figure 14:
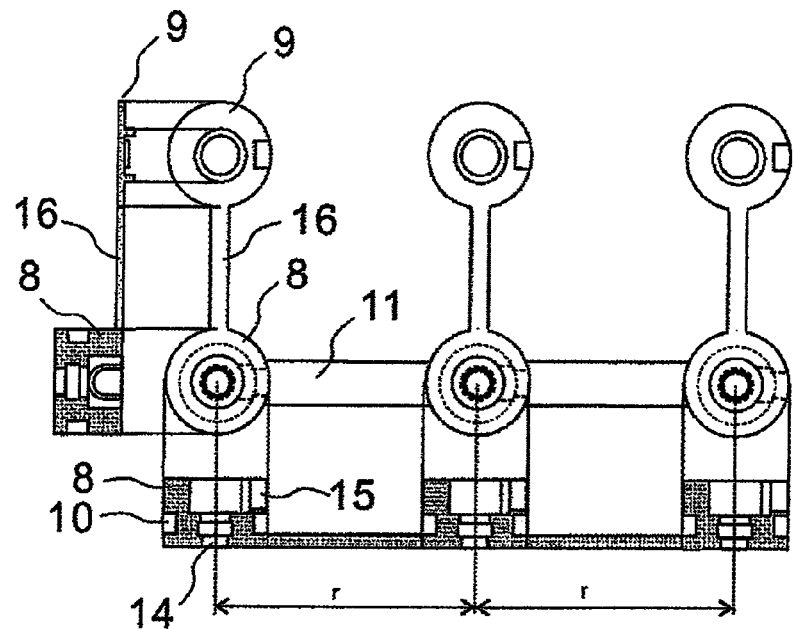
FIG. 14 is a sectional view of the components of FIG. 13.

FIG. 14 is one example of a sectional view of the components constituting the optical fiber fixing tool 1 and the fixing part 2 shown in FIGS. 13A to 13D. In this constitution, when the components are constituted of silicon rubber, not only the socket 8 and the base portion 11 but also the lid 9 can be integrally molded, and the characteristic that only one kind of molding die is required is provided. The retaining member 16 is molded at the same height as the top surface of the socket 8, and beyond the retaining member 16, the lid 9 is molded. As in FIG. 12, the tip end surface 12-1 of the optical fiber 12, which emits and receives light, is inserted into the optical fiber insertion port 14 opened in the lower portion of the socket 8, and the optical fiber is fixed so that the tip end surface 12-1 is at substantially the same height as the bottom surface of the socket 8, or is slightly (1 mm or less) projected from the bottom surface. The optical fiber of which end surface is inserted in the fiber insertion port 14 is bent in the socket 8, and is led outside from the optical fiber lead-out port 15. From above this, the optical fiber 12 is fixed with the lid 9. Recesses and projections may be formed in accordance with the shape of the optical fiber inside the fiber insertion port 14 and the fiber lead-out port 15 so that the optical fiber does not remove. A recess and a projection may be formed in the lid 9 so that the lid 9 hardly slips or removes when it is fitted in the socket 8. Further, the socket 8 and the lid 9 may be bonded to each other.

Figure 17A:
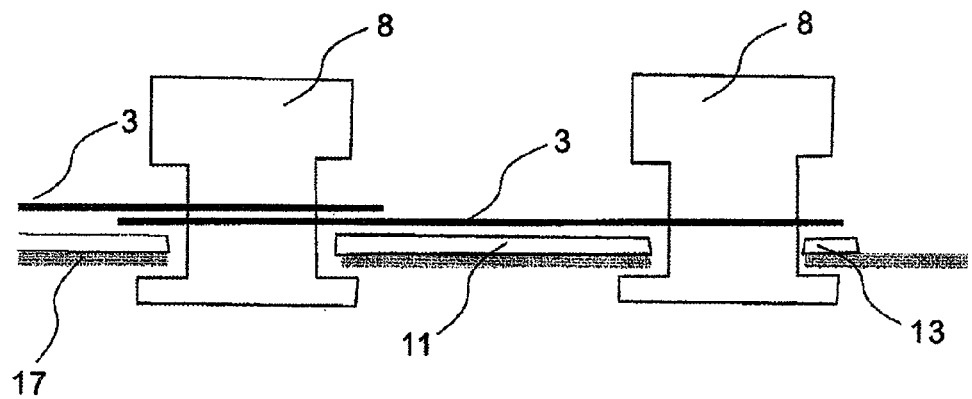
FIGS. 17A to 17C are sectional views showing a socket of the optical fiber fixing tool, a ring and the constitution of the connecting member of the embodiment of FIGS. 15A and 15B.
Figure 17B:
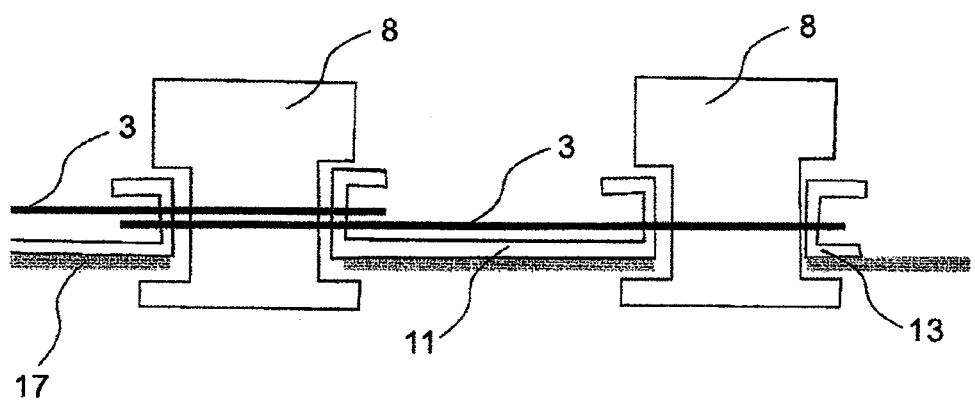
Figure 17C:
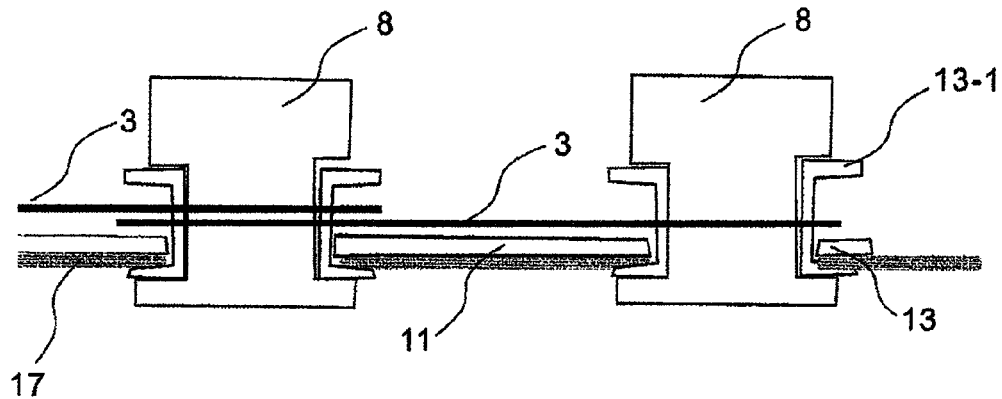

FIGS. 15A and 15B are conceptual views showing one example of the shapes of components constituting the biological optical measurement probe which is another embodiment of the present invention. FIG. 15A shows that the base portions 11 of the fixing parts are bonded to a cap 17 made of a material with elasticity. The material with elasticity is, for example, cloth with elasticity. In this case, the three rings 13 in which the single optical fiber fixing tools 7 can be inserted are placed on the base portion 11 instead of the sockets 8. As shown in FIG. 15B, the rings 13 on the adjacent base portions 11 are connected by the connecting members 3 so that the connecting members 3 are constituted to be rotatable around the rings 13. As the means, the ring 13 and the ring of the connecting member 3 may be fitted together in a groove 10 of the optical fiber fixing tool 7 as shown in FIG. 17A, or a groove-shaped fixing portion in which the connecting member 3 can be fitted may be provided in the ring 13 as shown in FIG. 17B. Further, as shown in FIG. 17C, a component 13-1 which is separate from the ring 13, and into which the ring 13 and the ring of the connecting member 3 are fitted and fixed may be prepared. Electrodes for EEG may be attached to a part or a plurality of parts of the material with elasticity.

Figure 15:
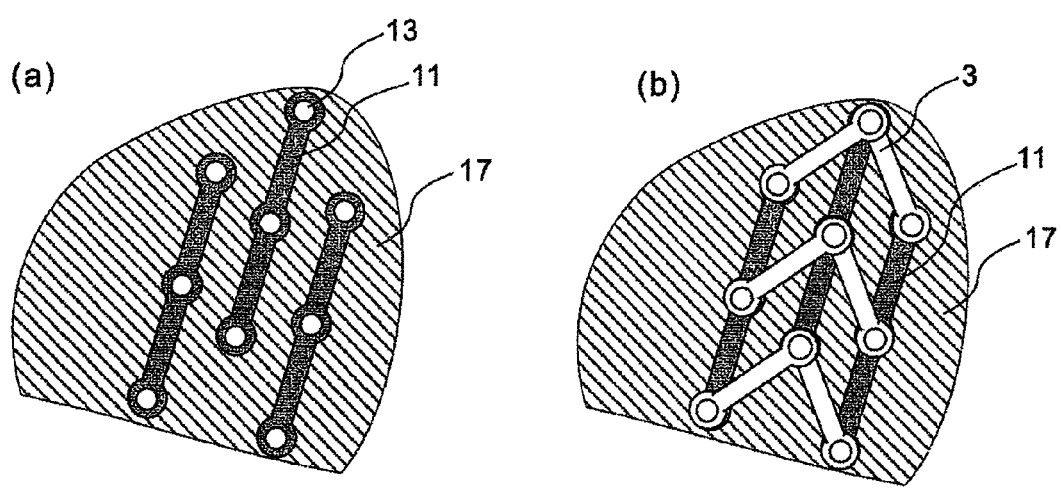
FIGS. 15A and 15B are conceptual views of a state in which a base portion is bonded to a cap of a material with elasticity (FIG. 15A), and a state in which the connecting members are further attached (FIG. 15B) of an embodiment using the material with elasticity of the probe according to the present invention.
Figure 16:
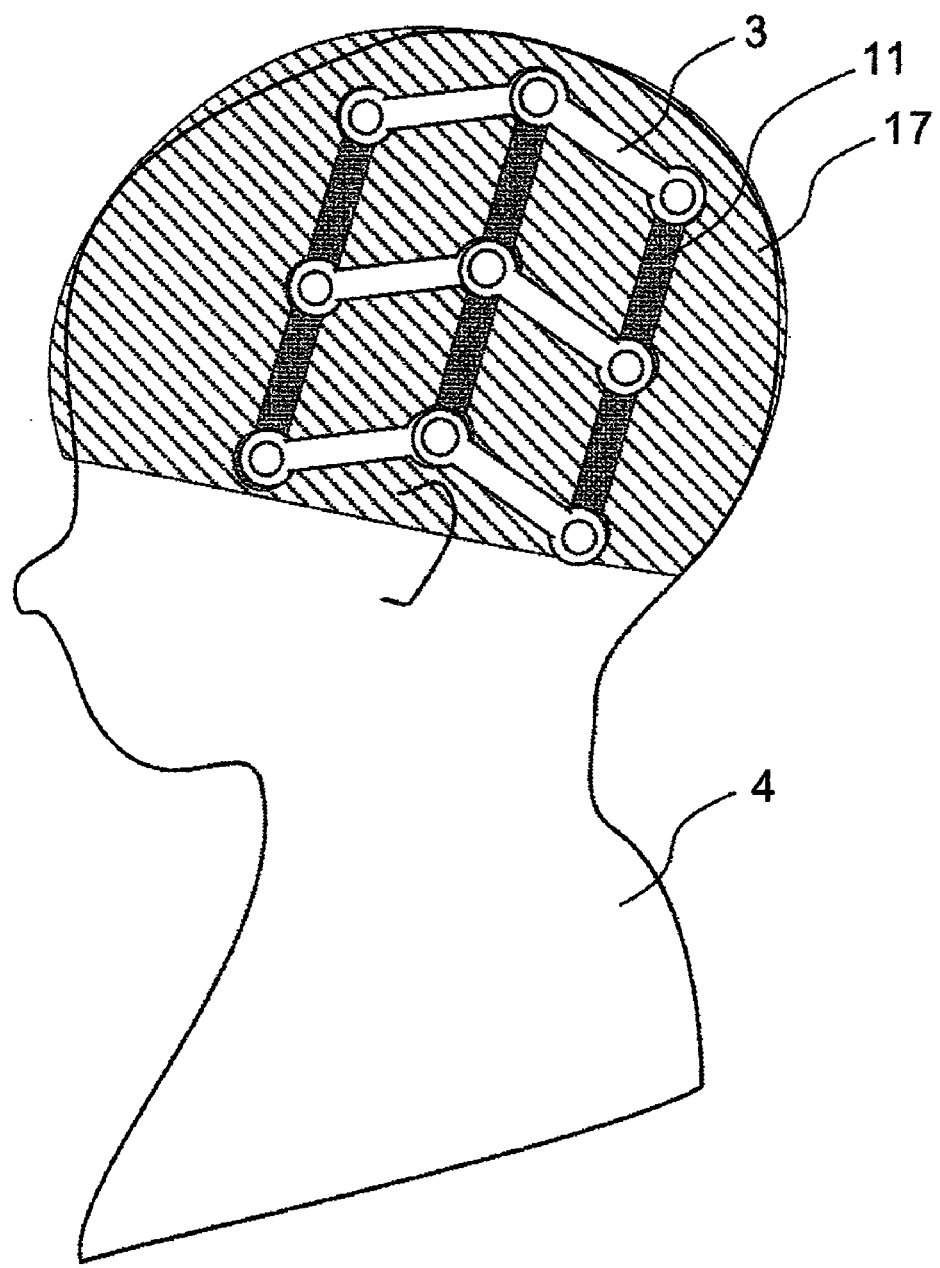
FIG. 16 is a view showing a state in which the probe of FIGS. 15A and 15B is fitted to a subject.

FIG. 16 shows a state in which the probe of FIGS. 15A and 15B is fitted to the subject 4. The cap 17 of the material with elasticity expands, and with this, the connecting members 3 rotate around substantially the centers of the rings 13 in which the sockets 8 are inserted to enlarge the gaps between the base portions 11. Since the materials of the base portion 11 and the connecting member 3 have almost no elasticity, the portions where the base portions 11 are bonded do not expand, and the probe can be fitted to heads of various sizes with a substantially constant distance kept between the rings 13 on the adjacent base portions 11 connected by the connecting member 3.

FIGS. 17A to 17C show sectional views showing the positional relationship of the socket 8, the ring 13 of the base portion 11 and the connecting member 3. In FIG. 17A, the ring 13 and the connecting member 3 are fastened by inserting the socket 8. The connecting member 3 rotates around the socket 8. FIG. 17B shows an embodiment in which the ring 13 has a projection for retaining the connecting member. The connecting member 3 is fitted in the projection portion of the ring 13, and rotates around the projection portion of the ring 13. In FIG. 17C, the connecting member 3 is retained by using the component 13-1 into which the ring 13 and the ring of the connecting member 3 are fitted and fixed. The connecting member 3 rotates around the component 13-1.

Figure 18:
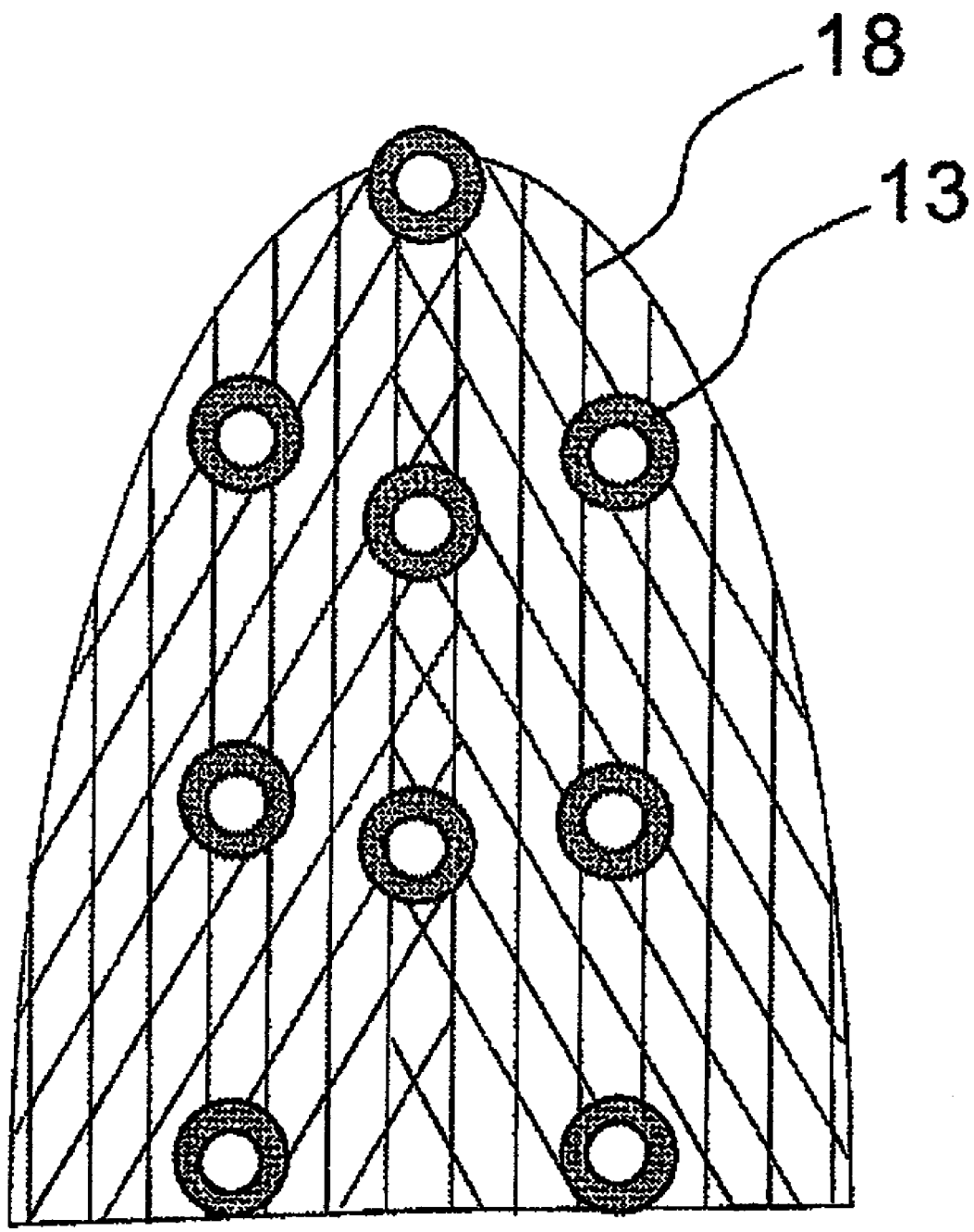
FIG. 18 is a conceptual view of an embodiment using a resin net material of the probe according to the present invention.

FIG. 18 shows a probe using a resin net (netlon) instead of the material 18 with elasticity of FIG. 15. The resin net expands and contracts in a fixed direction, but does not expand in the other directions. The portions in the direction in which the resin net does not expand are used as the base portions 11, and the rings 13 are equidistantly fixed in the direction in which the resin net does not expand. The distance is two or three centimeters which is similar to the above embodiments. In the portions where the directions of the base portions 11 do not match with each other, a plurality of pieces of the resin net may be connected to each other and used by switching the direction as shown in FIG. 18. Electrodes for EEG may be attached to a part or a plurality of parts of the net.

Figure 19:
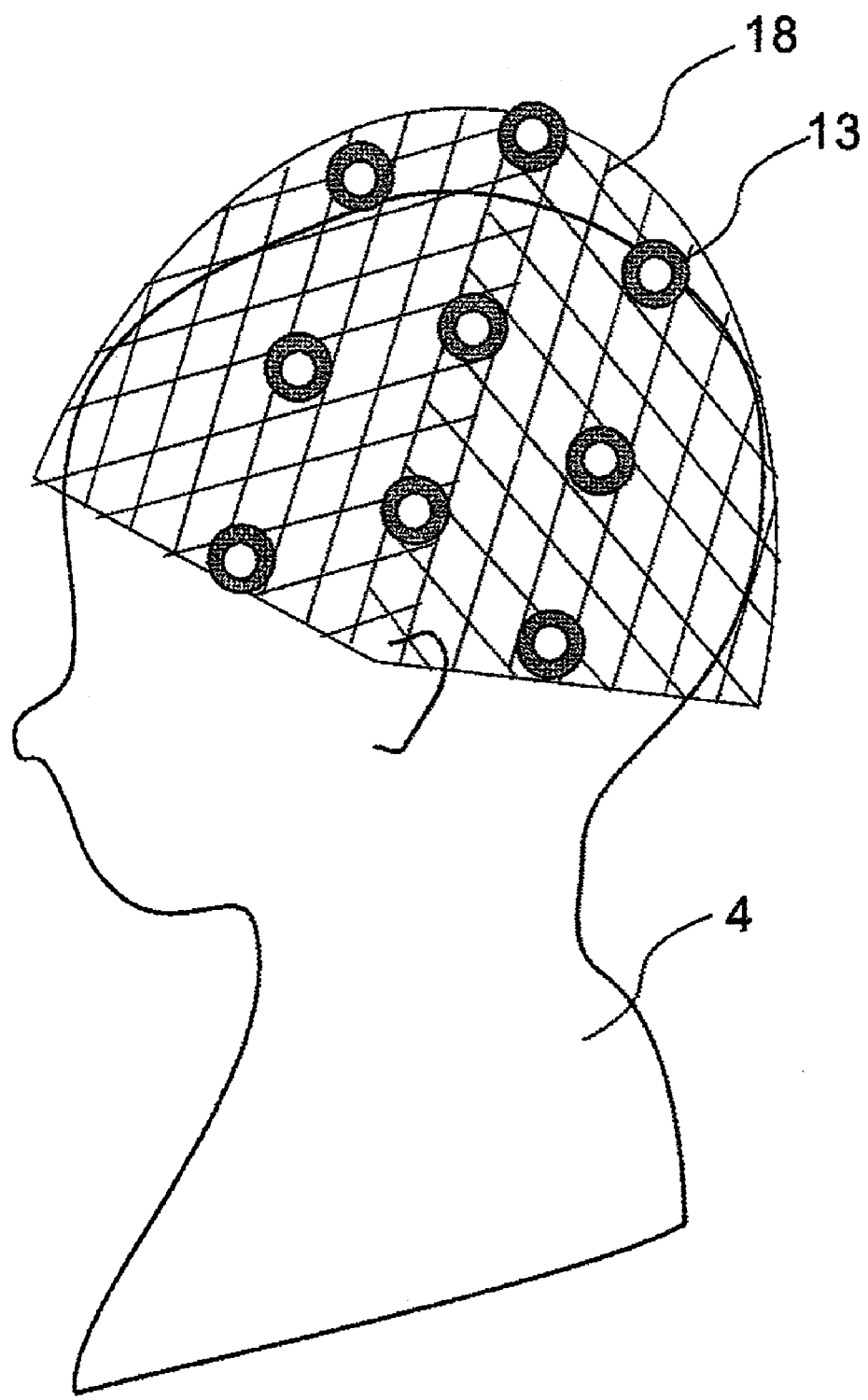
FIG. 19 is a view showing a state in which the probe of FIG. 18 is fitted to a subject.

FIG. 19 shows a state in which the probe of FIG. 18 is fitted to the subject 4. The function is the same as that of FIG. 16.

Figure 20:
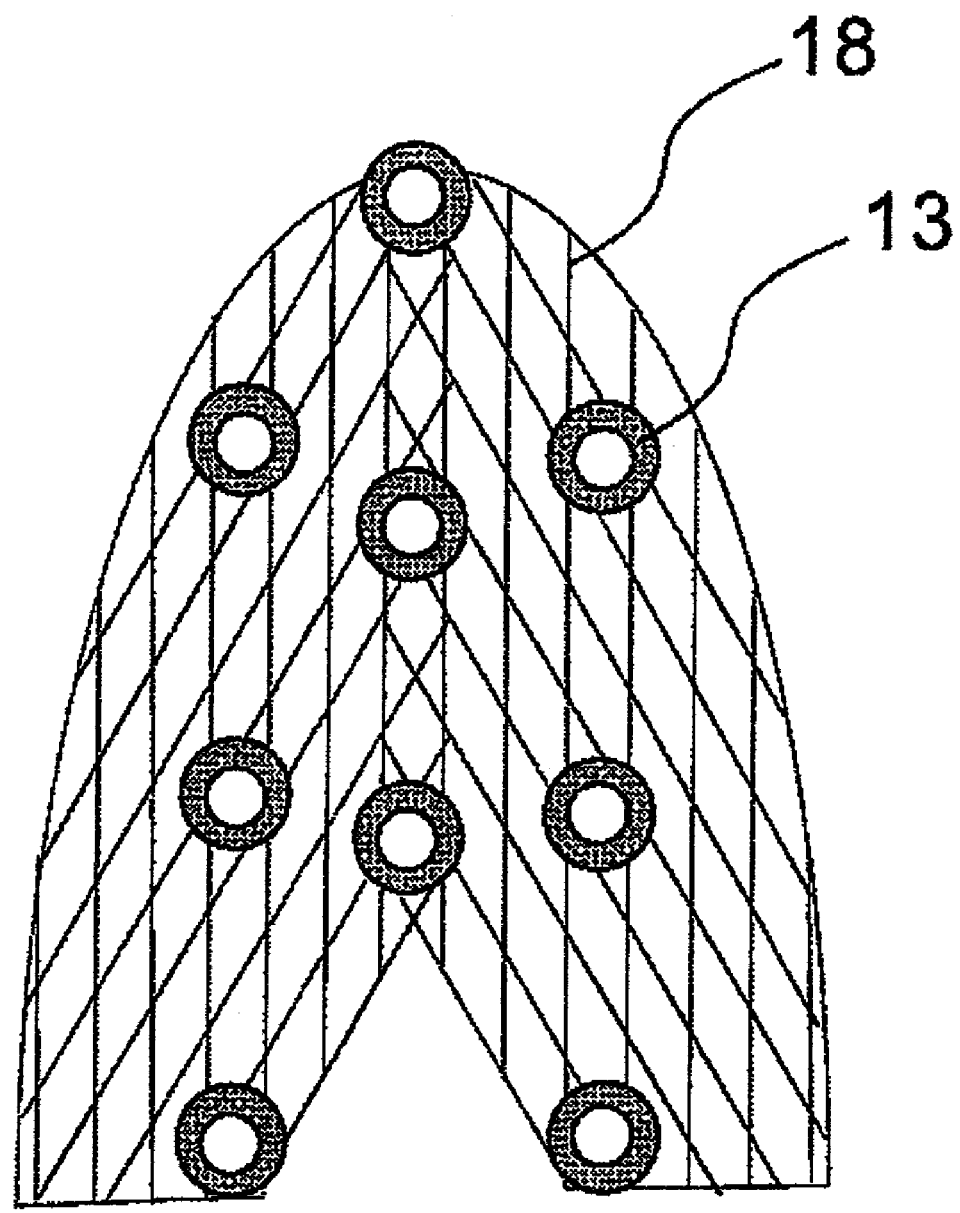
FIG. 20 is a conceptual view of another embodiment using a resin net material, of the probe according to the present invention.

FIG. 20 shows a probe using the resin net of FIG. 18, which can be fitted by avoiding ears, for example, by cutting off the portion of the net which is not used.

Figure 21:
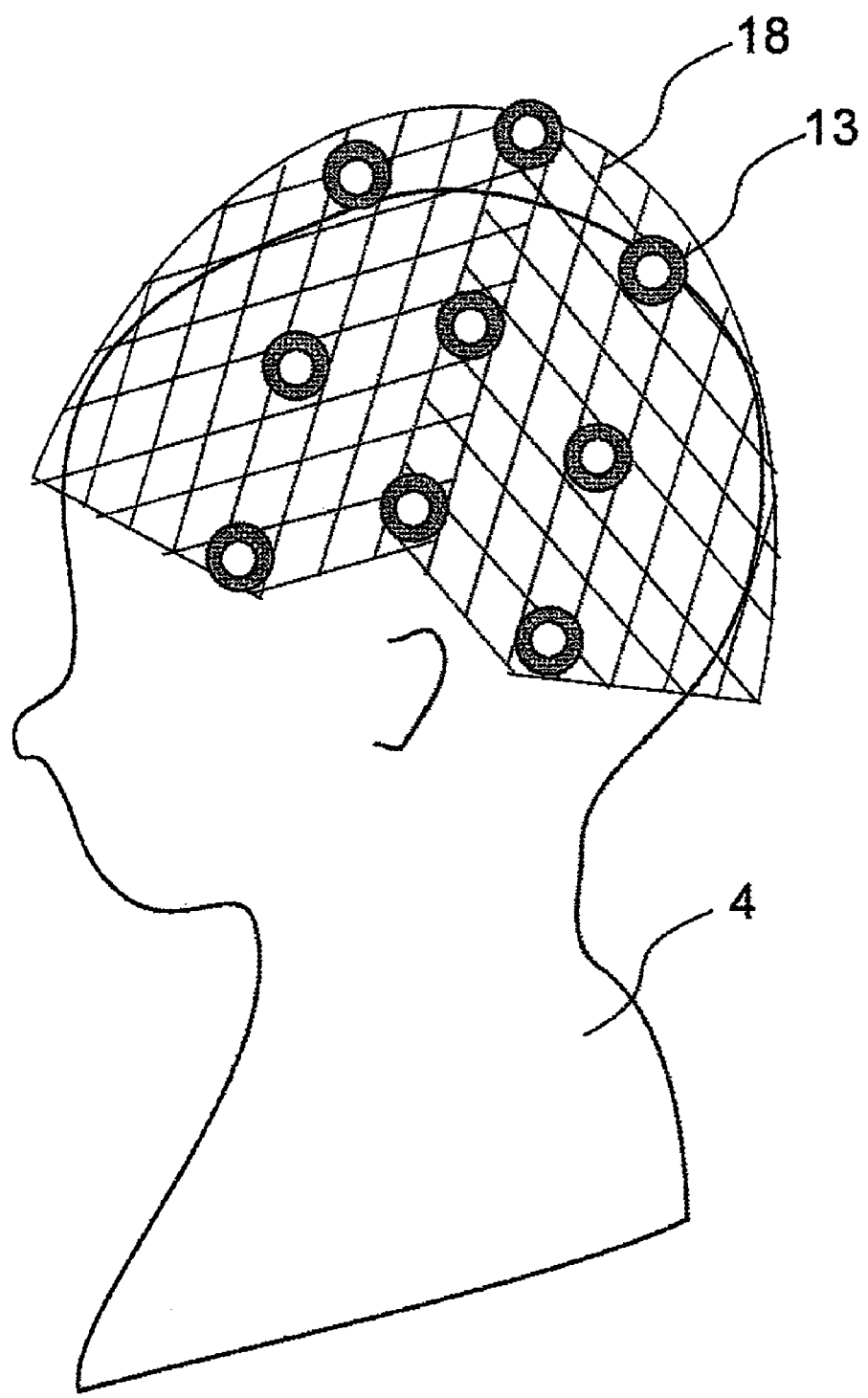
FIG. 21 is a view showing a state in which the probe of FIG. 20 is fitted to a subject.

FIG. 21 shows a state in which the probe of FIG. 20 is fitted.

Figure 22:
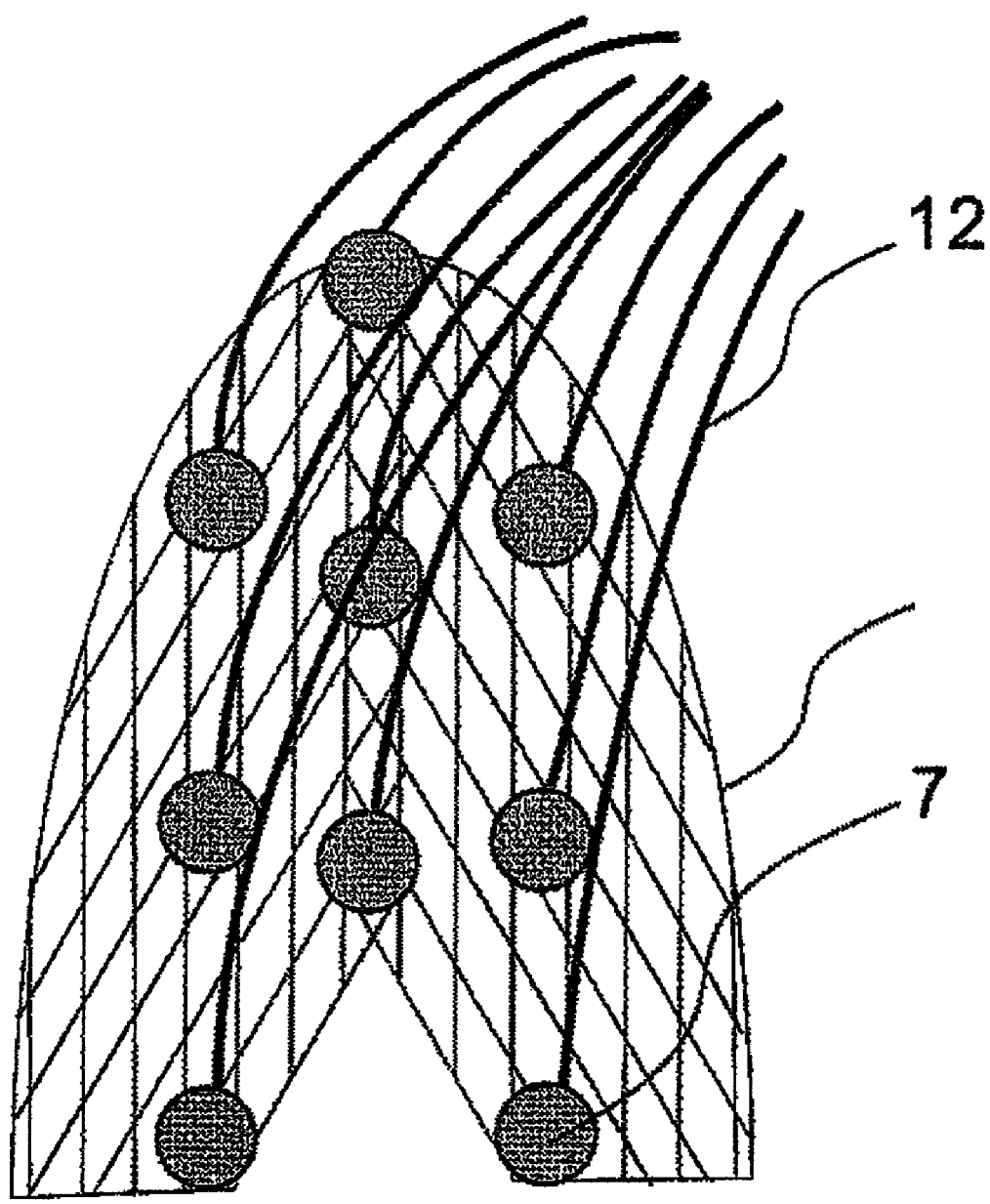
FIG. 22 is a conceptual view of still another embodiment using a resin net material, of the probe according to the present invention.

FIG. 22 shows a constitution in which the portions in the direction in which the resin net does not expand are used as the base portions 11, and in addition, meshes of the net are further used in place of the rings 13. The independent optical fiber fixing tools are directly inserted into the meshes of the net and used. At this time, the distance between the meshes for insertion in the direction in which the net does not expand is set at two or three centimeters.

Figure 23:
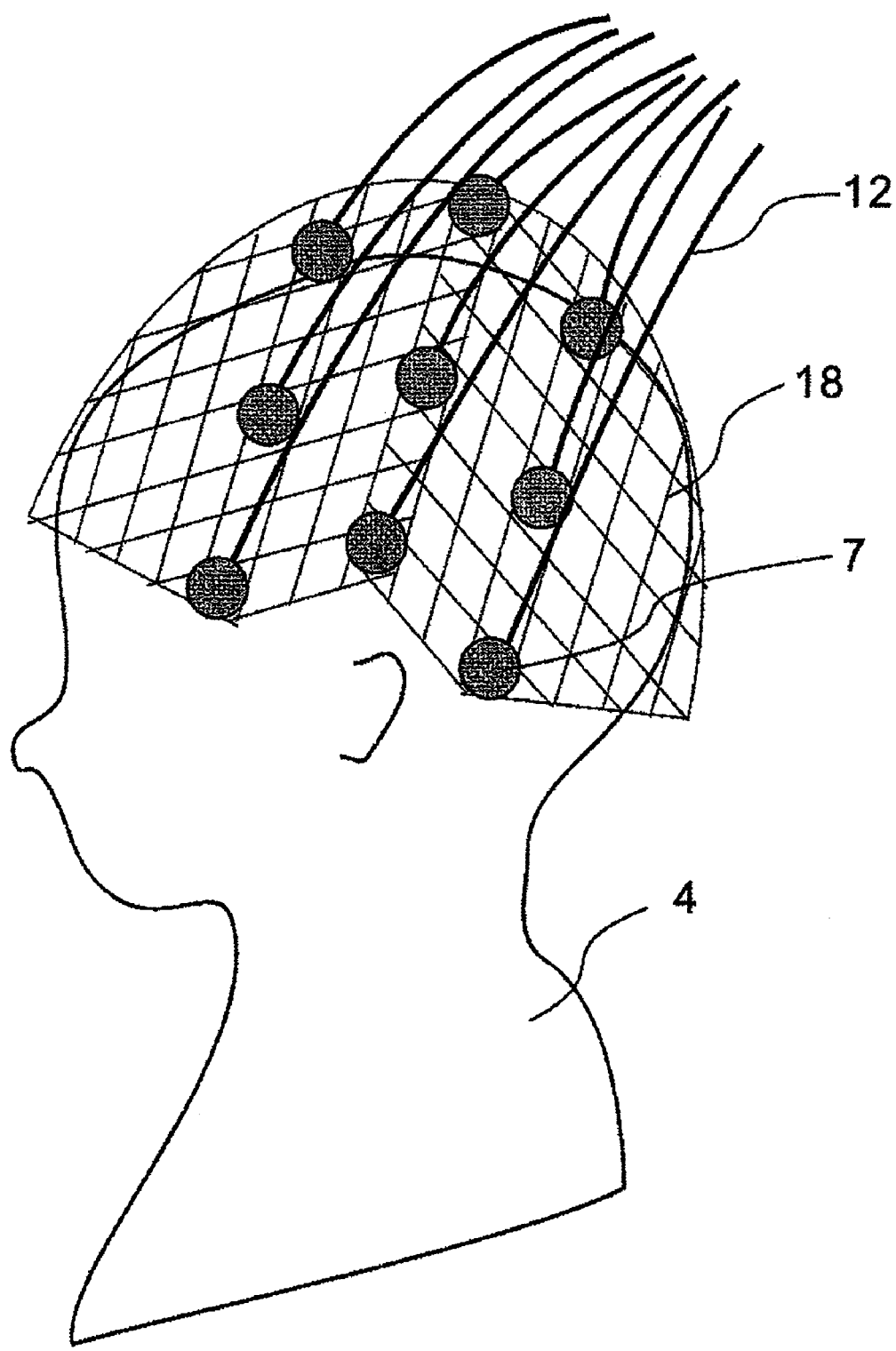
FIG. 23 is a view showing a state in which the probe of FIG. 22 is fitted to a subject.

FIG. 23 shows a state in which the probe of FIG. 22 is fitted to the subject 4.

As described in detail above, according to the present invention, the biological optical measurement probe can be realized, which is capable of adjusting positions in accordance with the size of the head part of a subject without changing the distance between an incident point and a detection point, capable of relatively measuring the same region even when the size changes, has high reproducibility of the measurement position, is easy to fit and capable of measuring the entire head part.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:
1. A biological optical measurement probe to be used on a subject, comprising:
   a plurality of emitting optical fibers for irradiating the subject with respective lights;

a plurality of detecting optical fibers for detecting respectively the lights emitted from the emitting optical fibers and passing through the subject;

a plurality of single optical fiber holders, wherein each of the plurality of single optical fiber holdersholds one of the emitting optical fibers or the detecting optical fibers;

a plurality of holding parts, wherein each of the plurality of holding parts includes at least three concatenated optical fiber holders, and wherein one of the emitting optical fibers or detecting optical fibers is fixed onto each of the at least three concatenated optical fiber holders; and connecting members, wherein each of the connect n members connects a pair of the concatenated optical fiber holders of the respective holding parts adjacent to each other, a pair of single optical fiber holders adjacent to each other or a air of a concatenated optical fiber holder and a smile optical fiber holder adjacent to each other, wherein the concatenated optical fiber holders of each of the holding parts are fixed at even distances along a straight line on each of the holding parts, wherein each of the connecting members is rotatable on a corresponding one of the single optical fiber holders or correcting one of the concatenated optical fiber holders, and wherein the holding parts form four sets of holding parts, the holding parts of each of the four sets being parallel to each other and extending towards a head top of the subject.

2. The biological optical measurement probe according to claim 1, wherein each of the connecting members is capable of being prevented from rotating on the corresponding one of the optical fiber holders.

3. The biological optical measurement probe according to claim 1, wherein each of the holding parts includes at least three of the optical fiber holders.

4. The biological optical measurement probe according to claim 1, wherein the holding parts extend to be parallel to each other.

5. The biological optical measurement probe according to claim 1, wherein the holding parts of the four sets extend radially when the probe is expanded along a plane.

6. The biological optical measurement probe according to claim 1, wherein the holding parts are fixed to a stretchy sheet.

7. The biological optical measurement probe according to claim 1, wherein each of the holding parts is formed on a yarn of resin mesh extending in a non-stretchy direction of the mesh.

8. A biological optical measurement instrument to be used on a subject, comprising:

a plurality of emitting optical fibers for irradiating the subject with respective lights;

a plurality of detecting optical fibers for detecting respectively the lights emitted from the emitting optical fibers and passing through the subject;

a plurality of single optical fiber holders.

wherein each of the plurality of single optical fiber holders holds one of the emitting optical fibers or the detecting optical fibers;

a plurality of holding parts, wherein each of the plurality of holding parts includes at least three concatenated optical fiber holders, and wherein one of the emitting optical fibers or detecting optical fibers is fixed onto each of the at least three concatenated optical fiber holders; and connecting members, wherein each of the connecting members connects a pair of the concatenated optical fiber holders of the respective holding parts adjacent to each other, a pair of single optical fiber holders adjacent to each other, or a air of a concatenated optical fiber holder and a single optical fiber holder adjacent to each other, wherein the concatenated optical fiber holders of each of the holding parts are fixed at even distances along a straight line on each of the holding parts, wherein each of the connecting members is rotatable on a corresponding one of the single optical fiber holders or correcting one of the concatenated optical fiber holders, and wherein the holding parts form four sets of holding parts, the holding parts of each of the four sets being parallel to each other and extending towards a head top of the subject.

9. The biological optical measurement instrument according to claim 8, wherein each of the connecting members is capable of being prevented from rotating on the corresponding one of the optical fiber holders.

10. The biological optical measurement instrument according to claim 8, wherein each of the holding parts includes at least three of the optical fiber holders.

11. The biological optical measurement instrument according to claim 8, wherein the holding parts extend to be parallel to each other.

12. The biological optical measurement instrument according to claim 8, wherein the holding parts of the four sets extend radially when the probe is expanded along a plane.

13. The biological optical measurement instrument according to claim 8, wherein the holding parts are fixed to a stretchy sheet.

14. The biological optical measurement instrument according to claim 8, wherein each of the holding parts is formed on a yarn of resin mesh extending in a non-stretchy direction of the mesh.

* * * * *